United States Patent
Chen et al.

(10) Patent No.: US 12,364,871 B2
(45) Date of Patent: Jul. 22, 2025

(54) BIOSTIMULATOR HAVING ARTICULATION

(71) Applicant: Pacesetter, Inc., Sylmar, CA (US)

(72) Inventors: Xiangqun Shawn Chen, Santa Clarita, CA (US); Tyler J. Strang, Valencia, CA (US); Bernhard Arnar, Minnetrista, MN (US); Kyle J. Nix, Arcadia, CA (US); Nicole Cooper, Burbank, CA (US); Keith Victorine, Santa Clarita, CA (US); Steve Chantasirivisal, Los Angeles, CA (US)

(73) Assignee: PACESETTER, INC., Sylmar, CA (US)

( * ) Notice: Subject to any disclaimer, the term of this patent is extended or adjusted under 35 U.S.C. 154(b) by 588 days.

(21) Appl. No.: 17/712,020

(22) Filed: Apr. 1, 2022

(65) Prior Publication Data
US 2023/0310868 A1 Oct. 5, 2023

(51) Int. Cl.
*A61N 1/375* (2006.01)
*A61N 1/05* (2006.01)

(52) U.S. Cl.
CPC ......... *A61N 1/3756* (2013.01); *A61N 1/0573* (2013.01); *A61N 1/37518* (2017.08); *A61N 1/3754* (2013.01); *A61N 1/37512* (2017.08)

(58) Field of Classification Search
CPC ............... A61N 1/3756; A61N 1/0573; A61N 1/37518; A61N 1/3754; A61N 1/37512; A61N 1/37205; A61N 1/362; A61N 1/0563; A61N 1/057
See application file for complete search history.

(56) References Cited

U.S. PATENT DOCUMENTS

| | | | |
|---|---|---|---|
| 8,670,842 B1 | 3/2014 | Bornzin et al. | |
| 2007/0135882 A1* | 6/2007 | Drasler | A61B 5/6848 607/32 |
| 2009/0018599 A1* | 1/2009 | Hastings | A61N 1/372 607/32 |
| 2009/0082827 A1* | 3/2009 | Kveen | A61N 1/37518 607/36 |
| 2012/0116489 A1* | 5/2012 | Khairkhahan | A61N 1/37518 607/127 |
| 2016/0310723 A1 | 10/2016 | Eggen et al. | |

OTHER PUBLICATIONS

Extended European Search Report from related European Patent Application No. 23165766.9, mailed on Aug. 2, 2023, 5 pages.
Extended European Search Report from related European Patent Application No. 24186975.9, mailed on Oct. 4, 2024, 5 pages.

* cited by examiner

*Primary Examiner* — Eugene T Wu
(74) *Attorney, Agent, or Firm* — WOMBLE BOND DICKINSON (US) LLP

(57) ABSTRACT

A biostimulator and a biostimulator system for septal pacing, is described. The biostimulator includes an articulation to allow an electrode axis of a pacing electrode to be directed differently than a housing axis of a housing. The housing contains electrical circuitry that is electrically connected to the pacing electrode. The differently directed axes allow the pacing electrode to affix to target tissue of an interventricular septal wall of a heart when the housing of the biostimulator is located near an apex of the heart. The articulation can include a flexible portion of an extension, a hinge, or a tether. Other embodiments are also described and claimed.

16 Claims, 13 Drawing Sheets

BIOSTIMULATOR HAVING ARTICULATION

BACKGROUND

Field

The present disclosure relates to biostimulators and related biostimulator systems. More specifically, the present disclosure relates to leadless biostimulators and related systems useful for septal pacing.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Leadless cardiac pacemakers incorporate electronic circuitry at the pacing site and eliminate leads, thereby avoiding shortcomings associated with conventional cardiac pacing systems. Leadless cardiac pacemakers can be anchored at the pacing site, e.g., in a right ventricle and, for dual-chamber pacing, in a right atrium, by an anchor. A delivery system can be used to deliver the leadless cardiac pacemakers to the target anatomy.

Cardiac pacing of the His-bundle is clinically effective and advantageous by providing a narrow QRS affecting synchronous contraction of the ventricles. His-bundle pacing in or near a membranous septum of a heart, however, has some drawbacks. The procedure is often long in duration and requires significant fluoroscopic exposure. Furthermore, successful His-bundle pacing cannot always be achieved. Pacing thresholds are often high, sensing is challenging, and success rates can be low.

Pacing at the left bundle branch (LBB) is an alternative to His-bundle pacing. Pacing at the LBB involves pacing past the His-bundle toward the right ventricle apex. More particularly, a pacing site for LBB pacing is typically below the His-bundle, on the interventricular septal wall near the tricuspid valve and pulmonary artery outflow track.

SUMMARY

Existing leadless pacemakers may not fit, or may interfere with heart structures, when placed at the pacing site for left bundle branch (LBB) pacing. More particularly, existing leadless pacemakers having bodies that are long and rigid and, when implanted at the interventricular septal wall, could extend into contact with the cardiac tissue of a ventricular free wall or the tricuspid valve. The long and rigid body of existing leadless pacemakers could also become tangled within chordae tendinae. Furthermore, a proximal end of the existing leadless pacemakers may flail within the heart chamber as the heart beats, causing cyclical contact with adjacent heart structures. Such contact could interfere with heart function. Thus, there is a need for a leadless biostimulator that can be engaged to the interventricular septal wall to pace the LBB without interfering with adjacent structures of the heart.

A biostimulator is described. In an embodiment, the biostimulator includes a pacing electrode and a housing. The pacing electrode may include a helical electrode or a post electrode, for example. The housing can contain pacing circuitry that is electrically connected to the pacing electrode to deliver pacing impulses through the pacing electrode to a target tissue. The pacing electrode and the housing have respective axes, e.g., a pacing electrode axis and a housing axis. The biostimulator includes an articulation to provide movement between the pacing electrode and the housing (or an anchor). For example, the articulation can be between the pacing electrode and the housing (or between the pacing electrode and an anchor) such that when the pacing electrode is affixed to an interventricular septal wall and the housing (or the anchor) is located at a ventricular apex, the electrode axis and the housing axis (or an anchor axis) extend in different directions. Accordingly, the pacing electrode can engage target tissue on an upper portion of the interventricular septal wall while the housing can be directed toward the ventricular apex without interfering with adjacent structures of the heart.

The biostimulator may include an anchor. The anchor can be mounted on the housing, e.g., on an attachment feature of the housing. Alternatively, the anchor may be mounted on a tether that extends proximally from the housing. The anchor can include several flexible tines arranged about the anchor axis. As described above, the anchor can be located at the ventricular apex when the pacing electrode is engaged to the septal wall tissue. Accordingly, the anchor can engage heart structures near the ventricular apex to secure and stabilize the housing in the downward direction, out of the way of the heart wall opposite to the septal wall and/or the heart valve leaflets.

The articulation can be a portion of the biostimulator that deforms, deflects, rotates, etc. For example, the biostimulator may include a flexible extension interconnecting the housing to the pacing electrode, and the articulation may be a flexible portion of the extension, e.g., a segment of the flexible extension. Alternatively or additionally, the articulation may include a hinge that connects the housing to a header assembly having the pacing electrode, and the hinge may rotate to provide relative movement between the housing and the pacing electrode. The biostimulator may include a tether that, like the flexible extension, includes a flexible segment to provide the articulation and relative movement between the pacing electrode and the housing or anchor. Accordingly, the articulation may be integrated in the biostimulator to join and provide relative movement between biostimulator structures such as the pacing electrode and the housing.

A biostimulator system is described. In an embodiment, the biostimulator system includes a biostimulator transport system. The biostimulator can be mounted on the biostimulator transport system to carry the biostimulator to or from the target anatomy. A method of left bundle branch pacing using the biostimulator and/or the biostimulator system is also described.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Embodiments describe a biostimulator and a biostimulator system for septal pacing. The biostimulator may, however, be used in other applications, such as deep brain stimulation. Thus, reference to the biostimulator as being a cardiac pacemaker for septal pacing is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator includes an articulation to allow an electrode axis of a pacing electrode to be directed differently than a housing axis of a housing. For example, the pacing electrode can be a helical electrode that affixes to an interventricular septal wall and the electrode axis can extend normal to the septal wall, while the housing can be located in a ventricular apex and the housing axis can be normal to an apex wall. Accordingly, when the fixation element is anchored in a septal wall of a heart, the housing can be located in the ventricular apex without interfering with a heart valve or an outer heart wall opposite to the septal wall. The biostimulator therefore fits well within the limited space of the target heart chamber. A biostimulator system is described that can transport the biostimulator to or from a pacing site at the septal wall.

Figure 1:
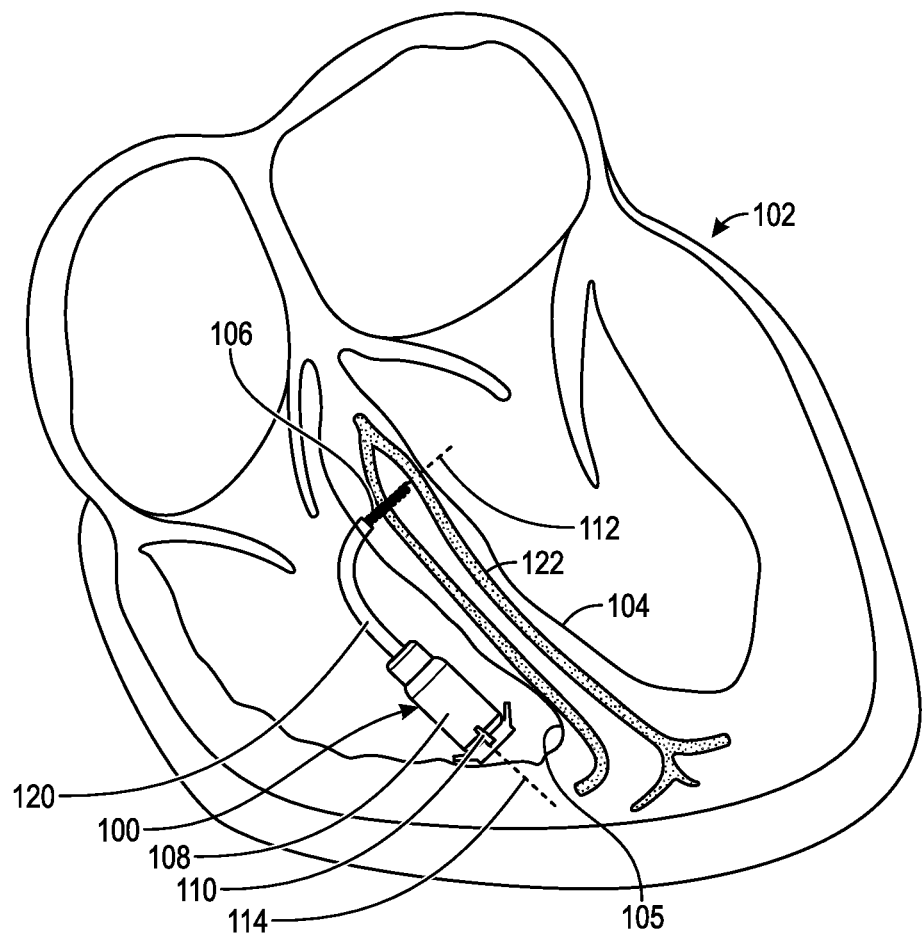
FIG. 1 is a diagrammatic cross section of a patient heart illustrating an example implantation of a biostimulator in a target anatomy, in accordance with an embodiment.

Referring to FIG. 1, a diagrammatic cross section of a patient heart illustrating an example implantation of a biostimulator in a target anatomy is shown in accordance with an embodiment. A leadless biostimulator system, e.g., a cardiac pacing system, includes one or more biostimulators 100. The biostimulators 100 can be implanted in a patient heart 102, and can be leadless (and thus, may be leadless cardiac pacemakers). Each biostimulator 100 can be placed in a cardiac chamber, such as a right atrium and/or right ventricle of the heart 102, or attached to an inside or outside of the cardiac chamber. For example, the biostimulator 100 can be attached to one or more of an interventricular septal wall 104 or a ventricular apex 105 of the heart 102. More particularly, the biostimulator 100 can be delivered to the septum, and one or more elements, such as a pacing electrode 106, can pierce the interventricular septal wall 104 of the septum to engage and anchor the biostimulator 100 to the tissue. Similarly, a housing 108 and/or an anchor 110 can be delivered into the ventricular apex 105.

The pacing electrode 106 can have an electrode axis 112, which is directed toward, e.g., normal to, the septal wall when the pacing electrode 106 is affixed to the septal wall. Similarly, the housing 108 can have a housing axis 114, which is directed toward, e.g., oblique to, an apex wall of the ventricular apex 105 when the housing 108 is located therein. When the pacing electrode 106 is affixed to the interventricular septal wall 104, and the housing 108 is located at the ventricular apex 105, the electrode axis 112 can extend in a different direction than the housing axis 114. For example, the electrode axis 112 can extend in a direction that is transverse or oblique to a direction of the housing axis 114. Accordingly, the pacing electrode 106 can be located to effectively probe and pace the left bundle branch 122, while the housing 108 can be placed in a safe and non-obstructive location within the heart chamber.

The non-coaxial relationship of the electrode axis 112 and the housing axis 114, which allows for safe and non-obstructive placement of the pacing electrode 106 and the housing 108, may be provided by an articulation 120 of the biostimulator 100. The articulation 120 can be located between the pacing electrode 106 and the housing 108. For example, as described below, the articulation 120 may be a flexible portion of the lead extension, a hinge, or any other mechanism that acts as a joint or juncture between a distal portion and a proximal portion of the biostimulator. More particularly, the articulation 120 may provide a movable joint between the portions to allow the biostimulator to articulate and conform to the target anatomy.

Leadless pacemakers or other leadless biostimulators 100 can be delivered to or retrieved from a patient using delivery or retrieval systems. The leadless biostimulator system can include delivery or retrieval systems, which may be catheter-based systems used to carry a leadless biostimulator 100 intravenously to or from a patient anatomy. The delivery or retrieval systems may be referred to collectively as transport systems, or biostimulator transport systems. Examples of transport systems are described below. In some implementations of biostimulator systems, a leadless pacemaker is attached, connected to, or otherwise mounted on a distal end of a catheter of the biostimulator transport system. The leadless pacemaker is thereby advanced intravenously into or out of the heart 102. The transport system can include features to engage the leadless pacemaker to allow fixation of the leadless pacemaker to tissue. For example, in implementations where the leadless pacemaker includes an active engaging mechanism, such as a helical fixation element, the transport system can include a docking cap or key at a distal end of the catheter, and the docking cap or key may be configured to engage the leadless pacemaker and apply torque to screw the active engaging mechanism into or out of the tissue. In other implementations, the transport system includes clips designed to match the shape of a feature on the leadless pacemaker and apply torque to screw the active engaging mechanism into or out of the tissue.

When the biostimulator 100 is delivered to and screwed into the septum of the heart 102, the pacing electrode 106 may be positioned for deep septal pacing at a target bundle branch 122 in the septum. For example, an active electrode of the pacing element can be positioned at the left bundle branch 122 in the septum. The biostimulator 100 may deliver pacing impulses through the pacing electrode 106 to the bundle branch(es).

Figure 2:
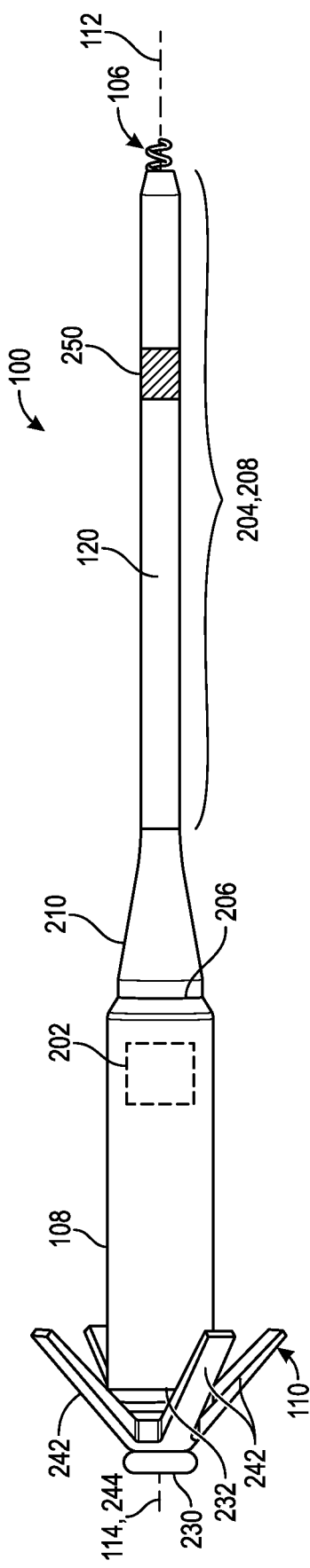
FIG. 2 is a side view of a biostimulator having an articulable extension, in accordance with an embodiment.

Referring to FIG. 2, a side view of a biostimulator having an articulable extension is shown in accordance with an embodiment. The biostimulator 100 can be a leadless cardiac pacemaker that can perform cardiac pacing and that has many of the advantages of conventional cardiac pacemakers while extending performance, functionality, and operating characteristics. In a particular embodiment, the biostimulator 100 can use two or more electrodes located on or within a housing 108 of the biostimulator 100 for pacing the cardiac chamber upon receiving a triggering signal from at least one other device within the body. The biostimulator 100 can have two or more electrodes, e.g., a portion of the pacing electrode 106 that acts as an active electrode and/or a portion of the housing 108 that acts as an active electrode. The electrodes can deliver pacing pulses to bundle branches 122 within the septum of the heart 102 to perform deep septal pacing, and optionally, can sense electrical activity from the muscle. The electrodes may also communicate bidirectionally with at least one other device within or outside the body.

In an embodiment, a leadless pacing system includes the biostimulator 100 having a flexible extended electrode. The flexible extended electrode includes the articulation 120, which allows the pacing electrode 106 to be located at the pacing site at a location on the septal wall nearer to the heart valve than the housing 108 while the housing 108 is located at the ventricular apex 105 for maximum stability.

The biostimulator 100 includes the housing 108 having a longitudinal axis, e.g., the housing axis 114. The housing 108 can contain a primary battery to provide power for pacing, sensing, and communication, which may include, for example, bidirectional communication. The housing 108 can optionally contain an electronics compartment 202 (shown by hidden lines) to hold circuitry adapted for different functionality. For example, the electronics compartment 202 can contain pacing circuitry for sensing cardiac activity from the electrodes, for receiving information from at least one other device via the electrodes, for generating pacing pulses for delivery to tissue via the pacing electrode 106, or other circuitry. The electronics compartment 202 may contain circuits for transmitting information to at least one other device via the electrodes and can optionally contain circuits for monitoring device health. The circuitry of the biostimulator 100 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Leadless pacemakers or other leadless biostimulators 100 can be fixed to an intracardial implant site, e.g., at the septal wall, by one or more actively engaging mechanism or fixation mechanism. For example, the fixation mechanism can include a screw or helical member that screws into the myocardium. In an embodiment, the pacing electrode 106 includes the fixation element. The pacing element can be coupled to the housing 108 by an extension 204. More particularly, the extension 204 extends between a housing distal end 206, at a distal end of the housing 108, and the pacing electrode 106.

In an embodiment, the extension 204 includes a flexible portion 208. The flexible portion 208 of the extension 204 can be the articulation 120 that allows for relative movement between the electrode axis 112 and the housing axis 114. More particularly, the axes 112, 114 may be coaxial in FIG. 2 when the flexible portion 208 is not bent, however, when the extension 204 is bent about the articulation 120 of the flexible portion 208 (FIG. 1) the axes of the pacing electrode 106 and the housing 108 become non-coaxial.

The articulation 120 may be any feature along the biostimulator 100 that allows for relative angular movement between the pacing electrode 106 and the housing 108 (or the anchor 110). As described below, the articulation 120 may include a mechanism, such as a hinge. In the case of a flexible portion of the biostimulator 100, however, such as the extension 204 or a tether (FIG. 18) the articulation can be a segment of material that deforms, deflects, or otherwise allows movement between a first boundary of the segment and a second boundary of the segment. For example, in the case of the flexible extension 204, a polymer jacket may extend longitudinally over the extension length. The polymer jacket may be flexible in that strain input during delivery can cause the polymer jacket to bend. More particularly, forces applied to the polymer jacket can cause strain and deflection of the flexible extension 204. A location of the deformation may be considered to be the articulation 110. Accordingly, the extension 204 can have one or more articulations when it is bent at one or more locations.

The extension 204 may include a structure that provides good torque transfer. For example, the flexible extension 204 can include fibers and/or cables that are woven, crosswound, interlaced, or otherwise configured to provide good transfer of torque from the housing distal end 206 to the pacing electrode 106 through the extension 204. Accordingly, torque can be transferred from a proximal end of the extension 204 to a distal end of the extension 204 at the pacing electrode 106 during device implantation. More particularly, torque may be applied at the housing 108 to screw the pacing electrode 106 into the myocardium. Alternatively, the flexible section of the extension 204 may be designed to turn independently of the housing 108 to facilitate engagement of the pacing electrode 106 to the myocardium after the housing 108 is located at the apex.

The biostimulator 100 may include a strain relief 210 between the housing distal end 206 and the extension 204. The strain relief 210 may be a separate component, or integrated with the extension 204. As described below, the strain relief 210 can be a tapered section that provides a transition to ease delivery by a transport system. More particularly, the strain relief 210 can effectively transfer torque and bending forces applied to the housing 108 by the transport system, to the extension 204.

In an embodiment, the biostimulator 100 includes an attachment feature 230. The attachment feature 230 can be mounted on a proximal housing end 232 of the housing 108. More particularly, the attachment feature 230 can be mounted on an opposite end of the housing 108 from the extension 204 and the pacing electrode 106, which as described above, can be coupled to the distal housing end 206 of the housing 108. The attachment feature 230 can facilitate precise delivery or retrieval of the biostimulator 100. For example, the attachment feature 230 can be formed from a rigid material to allow a delivery or retrieval system to engage the attachment feature 230 and transmit torque through the housing 108 and extension 204 to screw the pacing electrode 106 into the target tissue.

The biostimulator 100 may include the anchor 110 to affix or maintain the housing 108 at the apex. The anchor 110 may include, for example, several flexible tines 242 arranged about an anchor axis 244. As described further below, the flexible tines 242 can have a structure to facilitate interference between the tines 242 and heart structures that maintain the housing 108 in the apex region of the heart chamber.

Optionally, an anode 250 may be on the extension 204. More particularly, the anode 250 can be an anode ring, such as an annular band of metal, mounted on an outer surface of the extension 204. The anode 250 may be spaced proximally apart from the pacing electrode 106. More particularly, the anode ring can be at a predetermined distance from the electrode to provide for adequate electrical isolation between the pacing electrode 106 and the anode 250.

Figure 3:
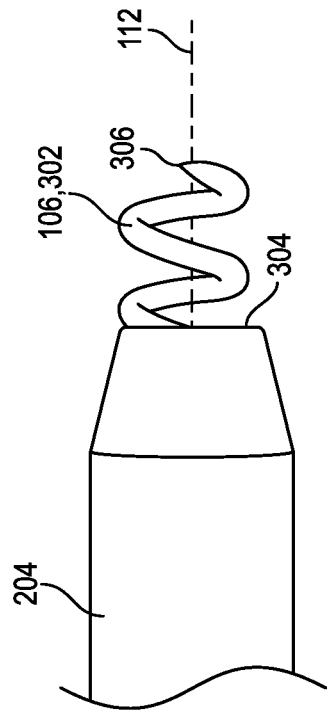
FIG. 3 is a side view of a pacing electrode of a biostimulator, in accordance with an embodiment.

Referring to FIG. 3, a side view of a pacing electrode of a biostimulator is shown in accordance with an embodiment. The biostimulator 100 can include the pacing electrode 106 coupled to the housing 108. The pacing electrode 106 can extend along, e.g., axially along or helically about, the longitudinal axis of the extension 204. For example, the pacing electrode 106 can include a helical electrode 302 extending about the electrode axis 112. The helical electrode 302 can include a wire or filament extending helically about the electrode axis 112. The helical electrode 302 can extend from an extension distal end 304 of the extension 204 to an electrode tip 306. Over its length, the helical electrode 302 can revolve about electrode axis 112. The helical pacing electrode 106 can screw into a target tissue. When the pacing electrode 106 engages the target tissue, the housing 108 can be advanced and/or rotated to cause the helical electrode 302 to anchor the biostimulator 100. Accordingly, the pacing electrode 106 may both pace the septal wall as well as affix the biostimulator 100 to the septal wall.

As described below, the pacing electrode 106 may alternatively be a prong electrode (FIG. 21) having a linear or conical element to pierce into the target tissue. Other electrode configurations are also contemplated. For example, the pacing electrode 106 may be a passive electrode or a tined electrode. Accordingly, the electrode structures described herein are provided by way of example and not limitation.

Figure 4:
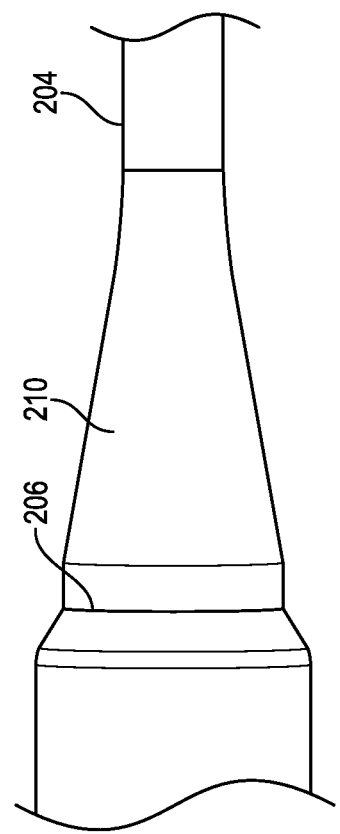
FIG. 4 is a side view of a strain relief of a biostimulator, in accordance with an embodiment.

Referring to FIG. 4, a side view of a strain relief of a biostimulator is shown in accordance with an embodiment. The strain relief 210 coupled to the housing distal end 206 can have a conical profile. More particularly, an outer dimension of the strain relief 210 at the housing distal end 206 may be greater than an outer dimension of the strain relief 210 at a transition into the extension 204. A stiffness of the strain relief 210 may reduce in a distal direction from the housing distal end 206. More particularly, a material or geometry of the strain relief 210 is such that flexibility of the strain relief 210 increases in a direction from the housing distal end 206 to the extension 204. Accordingly, the strain relief 210 can provide a gradual transition of stiffness between the housing 108 and the extension 204 to allow for effective torque transfer and pushability of the biostimulator 100.

Figure 5:
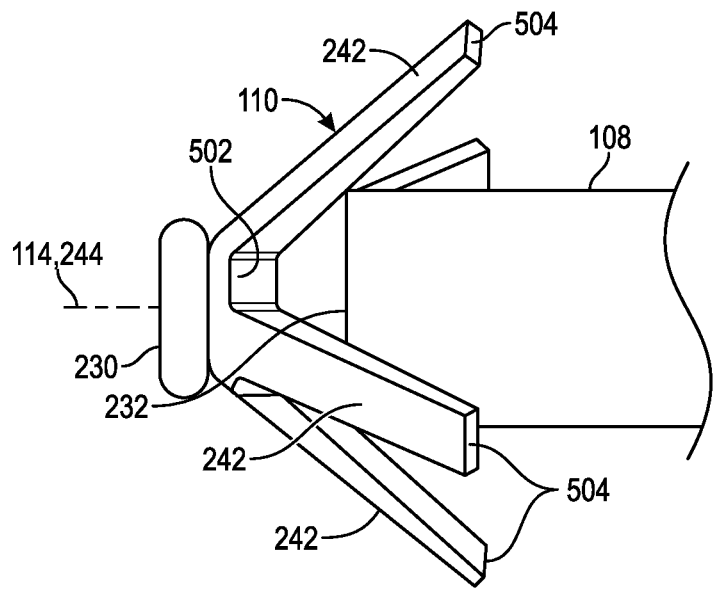
FIG. 5 is a side view of an anchor of a biostimulator, in accordance with an embodiment.

Referring to FIG. 5, a side view of an anchor of a biostimulator is shown in accordance with an embodiment. The anchor 110 of the biostimulator 100 may be mounted on the housing 108. For example, the anchor 110 may include a collar 502, e.g., an annular element, coaxial with and mounted on a stem of the attachment feature 230. The stem can be a reduced diameter section of the attachment feature 230 between a proximal portion that connects to the transport system and a distal portion that mounts on the housing proximal end 232. Accordingly, the collar 502 can fit between the proximal portion and the distal portion to secure the anchor 110 to the attachment feature 230 and/or housing 108. The anchor 110 can have the anchor axis 244, e.g., coaxial with the collar 502, and the anchor axis 244 may be coaxial with the housing axis 114.

In an embodiment, the anchor 110 includes several flexible tines 242 arranged about the anchor axis 244. Each tine 242 may extend radially outward from the collar 502. For example, two or more tines 242 may extend in an outward direction from the anchor axis 244 to respective tine tips 504 at a radially outward location. The tine tips may be distal to or proximal to a base of the tines 242. For example, the tine tips 504 may be distal to the collar 502, as shown in FIG. 5. Alternatively, the tines 242 may extend proximally to tine tips 504 that are proximal to the collar 502 and/or the attachment feature 230.

The tines 242 may be flexible to allow the tines 242 to deflect during delivery and/or implantation. For example, the tines 242 may flex backward during delivery to fit within a lumen of the transport system. Upon delivery, e.g., when the biostimulator 100 is advanced out of the transport system, the tines 242 can recover to a predetermined shape. For example, the tines 242 can spring forward to the distally directed shape shown in FIG. 5. During recovery, the tines 242 can entangle with and/or otherwise grip an anatomical structure, e.g., trabeculae carneae, within the heart 102 chamber. Accordingly, the flexible tines 242 can interact with inner surface structures of the ventricle to anchor and stabilize the housing 108 within the heart chamber.

Flexibility of the tines 242 may be provided by the material and/or structure of the tine 242. More particularly, at least a portion of the tines 242 may be formed from a flexible material such as a soft, molded silicone. Alternatively, the flexible tines 242 may be formed from a shape memory material, such as super elastic nickel titanium. The tines 242 may have a hybrid construction as well. For example, the flexible tines 242 could include a core material, such as metal wires, that are overmolded with or coated by an implantable polymer, such as an elastomer material. Accordingly, the tines 242 may be flexible enough to bend into the transport system and stiff enough to hold the housing 108 in place within the heart chamber.

Figure 6:
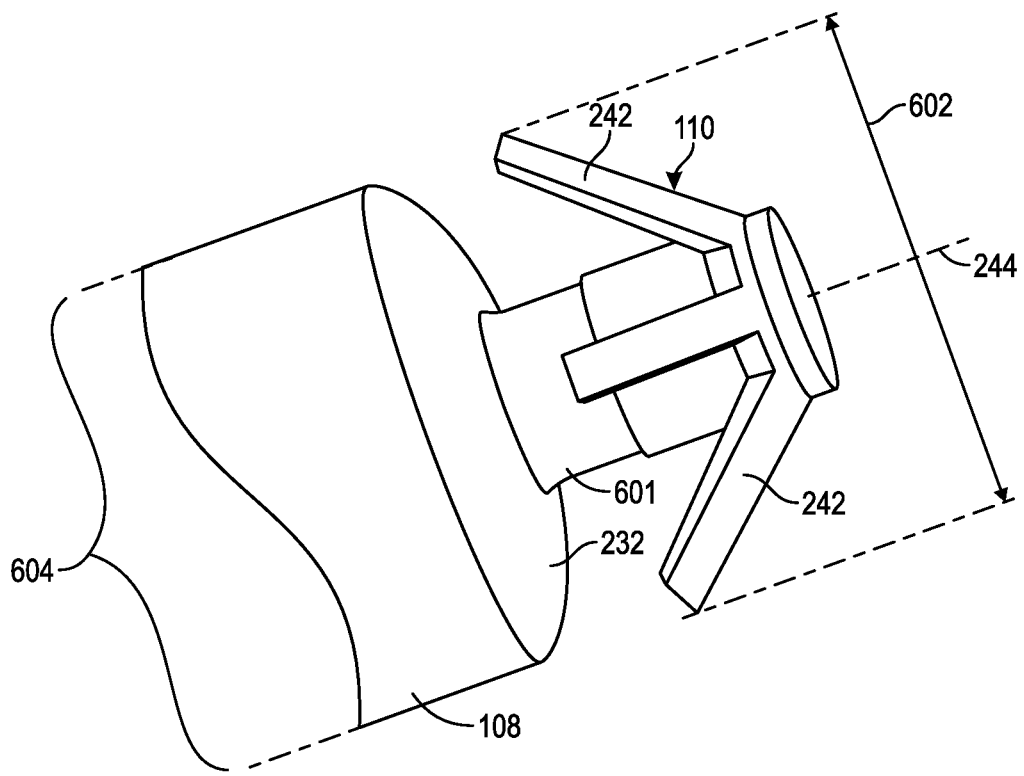
FIG. 6 is a side view of an anchor of a biostimulator, in accordance with an embodiment.

Referring to FIG. 6, a side view of an anchor of a biostimulator is shown in accordance with an embodiment. The tines 242 may extend outward from a structure other than the collar 502. In an embodiment, the anchor 110 includes an anchor post 601 extending proximally from the housing proximal end 232. For example, the anchor post 601 can extend along the anchor axis 244 in the longitudinal direction. Each of the flexible tines 242 can extend radially outward, either distally or proximally, from the anchor post 601. Accordingly, the flexible tines 242 of the anchor 110 structure can reach out to interfere with and grip anatomical structures within the heart 102 chamber to anchor 110 the housing 108 therein.

The flexible tines 242 can have an outer dimension that is less than or greater than an outer dimension of the housing 108. For example, referring again to FIG. 5, the flexible tines 242 extend radially outward from an outer dimension of the housing wall, and thus, the outer dimension of the tines 242 is greater than the outer dimension of the housing 108. By contrast, referring to FIG. 6, an anchor outer dimension 602 is equal to or less than a housing outer dimension 604. The anchor outer dimension 602 can balance the advantages of loading the biostimulator 100 into the transport system with a likelihood of gripping anatomical structures when deployed from the transport system. More particularly, when the anchor outer dimension 602 is equal to or less than the housing outer dimension 604, the anchor 110 may be more easily loaded into the transport system. When the anchor outer dimension 602 is greater than the housing outer dimension 604, however, the anchor 110 may be more likely to engage trabeculae carneae within the heart chamber.

Figure 7:
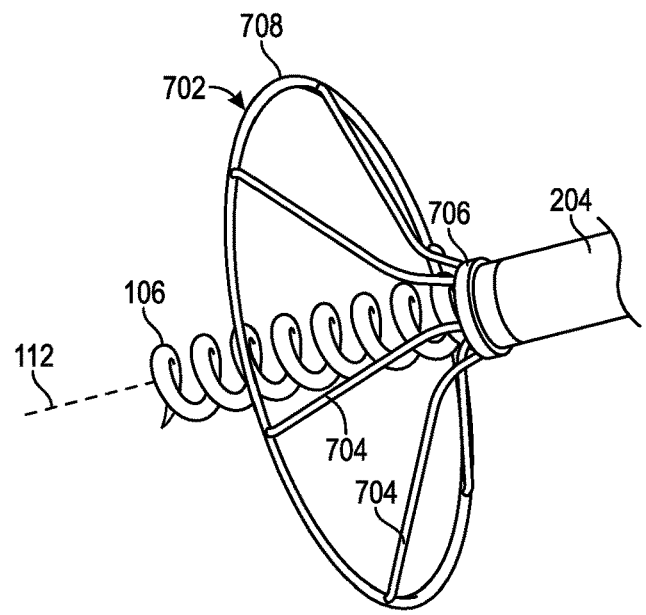
FIG. 7 is a side view of a stabilizer of a biostimulator, in accordance with an embodiment.

Referring to FIG. 7, a side view of a stabilizer of a biostimulator is shown in accordance with an embodiment. Stabilizing the pacing electrode 106 within the target tissue can the beneficial for several reasons. First, it may be advantageous to hold the pacing electrode 106 in a position such that the electrode axis 112 extends normal or perpendicular to the heart wall. The electrode may be more likely to reach and effectively pace the bundle branch 122 under such circumstances. Additionally, stabilizing the pacing electrode 106 within the heart tissue can reduce the likelihood that the electrode will back out of the tissue and lose effective contact with the bundle branch 122. In an embodiment, the biostimulator 100 includes a stabilizer 702 to engage the heart wall such that the pacing electrode 106 is oriented and maintained in an effective pacing position.

The stabilizer 702 may be mounted on the flexible extension 204 of the biostimulator 100. The stabilizer 702 can include one or more stabilizing elements 704 that extend radially outward from the extension 204. For example, the stabilizing elements 704 can extend in a distal direction and radially outward relative to the electrode axis 112 from a stabilizer mount 706. The stabilizer mount 706 can be positioned on an outer surface of the extension 204. The stabilizing elements 704 can extend to distal ends that directly contact the target tissue, or alternatively, the distal ends may connect to a stabilizer loop 708 that interconnects the distal ends and presses against the septal wall during implantation.

A profile of the stabilizer 702, as defined by the stabilizer elements 704 and the stabilizer loop 708, may be cupped or conical. More particularly, the profile can be concave in the distal direction. Accordingly, stabilizer 702 may include a cup structure, e.g., molded from silicone or an elastomeric material, rather than the framework structure, e.g., a shape memory wire structure, shown in FIG. 7. At least a portion of the stabilizer 702 may be radiopaque. For example, radiopaque marker bands may be located on the stabilizer loop 708.

In an embodiment, stabilizer 702 is movable along the flexible extension 204. For example, the stabilizer mount 706 may move longitudinally along the extension 204. Movement may be provided by a friction fit between the stabilizer mount 706 and an outer surface of the extension 204. For example, an axial load applied during implantation may be sufficient to cause the stabilizer 702 to slide along the extension 204. By contrast, the axial load applied to the stabilizer 702 after implantation by the beating heart 102 may be insufficient to cause relative motion between the stabilizer mount 706 and the extension 204.

Figure 8:
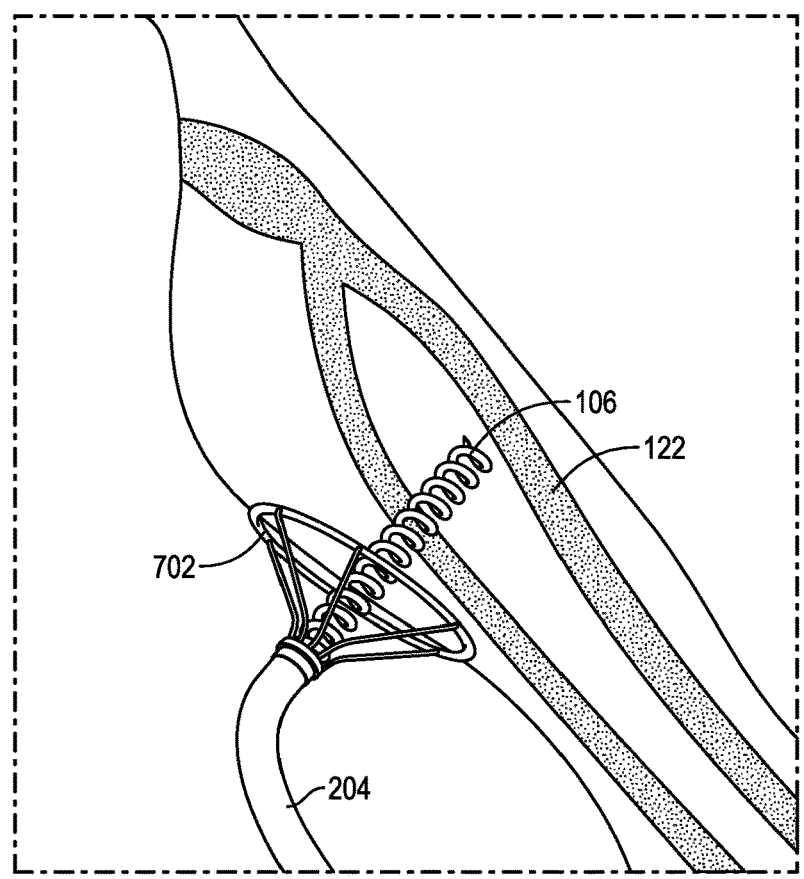
FIG. 8 is a pictorial view of a biostimulator having a stabilizer engaged to a target anatomy, in accordance with an embodiment.

Referring to FIG. 8, a pictorial view of a biostimulator having a stabilizer engaged to a target anatomy is shown in accordance with an embodiment. When the biostimulator 100 is engaged to the septal wall, pacing electrode 106 can extend into the heart tissue to contact the target bundle branch 122. During implantation, the stabilizer 702 can slide or move along the extension 204 to allow the pacing electrode 106 to be deployed to a desired depth within the target tissue. After implantation, the stabilizer 702 can press against the heart wall. Such pressure can maintain the orientation of the pacing electrode 106 in a generally perpendicular direction relative to the heart wall. More particularly, rather than the extension 204 weighing on and deflecting the pacing electrode 106 into a non-perpendicular orientation, the stabilizer 702 supports the pacing electrode 106 and relieves strain to maintain the pacing electrode position. Furthermore, the stabilizer 702 can apply some back pressure that pre-loads the pacing electrode 106 within the heart tissue to limit excessive movement of the pacing electrode 106 within the septal wall as the heart beats.

Figure 9:
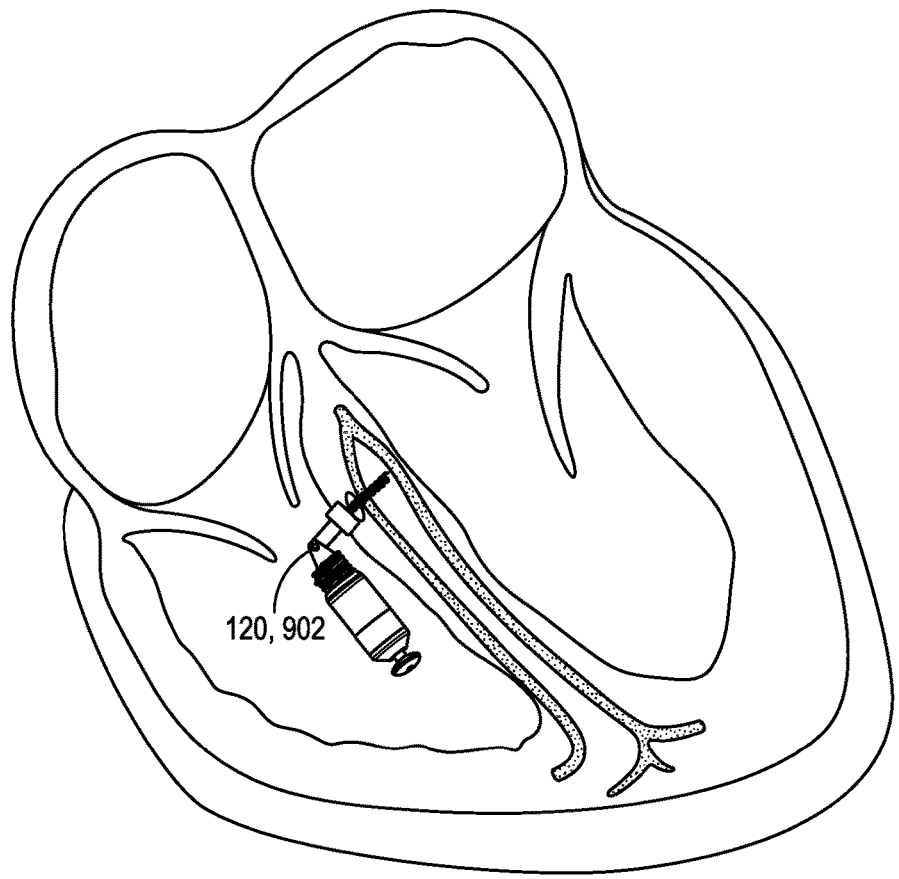
FIG. 9 is a diagrammatic cross section of a patient heart illustrating an example implantation of a biostimulator in a target anatomy, in accordance with an embodiment.

Referring to FIG. 9, a diagrammatic cross section of a patient heart illustrating an example implantation of a biostimulator in a target anatomy is shown in accordance with an embodiment. The articulation 120 of the biostimulator 100 may be provided by alternative structures. In an embodiment, the articulation 120 includes a hinge 902. As described below, the hinge 902 allows relative movement between a distal portion of the biostimulator 100 and the housing 108. Accordingly, the pacing electrode 106 can extend into the target tissue, e.g., perpendicular to the heart wall, and the housing 108 may be hinged downward and directed toward the apex of the heart 102 to take advantage of the space within the heart chamber without interfering with the opposite heart wall or heart valve.

Figure 10:
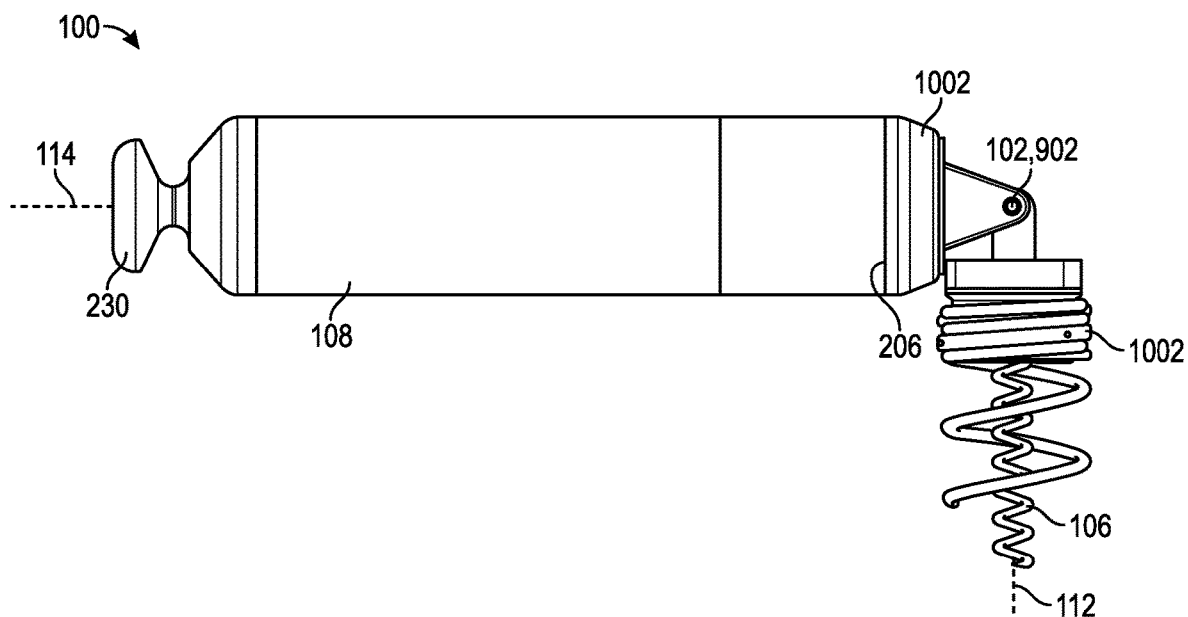
FIG. 10 is a side view of a biostimulator having an articulable hinge, in accordance with an embodiment.

Referring to FIG. 10, a side view of a biostimulator having an articulable hinge is shown in accordance with an embodiment. The hinge 902 can interconnect a body of the biostimulator 100 and the distal portion of the biostimulator 100, including the pacing electrode 106. The biostimulator 100 can include a header assembly 1002 that includes the hinge 902. More particularly, the header assembly 1002 can be coupled to the housing 108, e.g., at the housing distal end 206. The hinge 902 can allow a distal portion of the header assembly 1002 having the pacing electrode 106 to pivot or move with respect to a proximal portion of the header assembly 1002 that connects to the housing 108. Accordingly, the pacing electrode 106 of the header assembly 1002 can be directed toward the bundle branch 122 and the housing 108 can be directed toward the ventricular apex 105. More particularly, the hinge 902 can be articulated such that the electrode axis 112 can be directed differently, e.g., orthogonal to, the housing axis 114.

Figure 11:
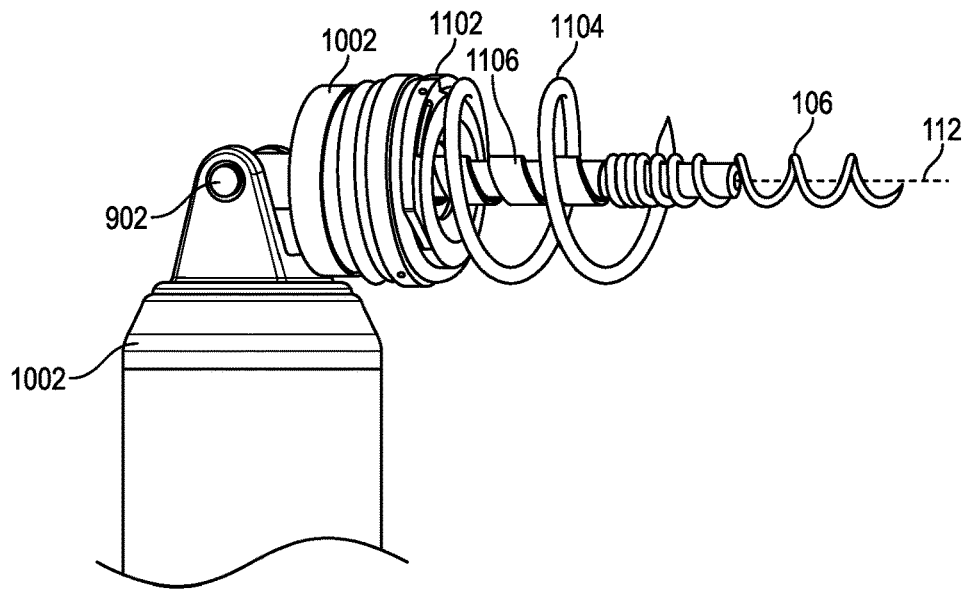
FIG. 11 is a front perspective view of a distal portion of a biostimulator having an articulable hinge, in accordance with an embodiment.

Referring to FIG. 11, a front perspective view of a distal portion of a biostimulator having an articulable hinge is shown in accordance with an embodiment. The articulable hinge 902 of the biostimulator 100 may be any of several known hinge configurations. For example, the hinge 902 can include a barrel hinge having a pin connecting the distal portion of the header assembly 1002 to the proximal portion of the header assembly 1002. The hinge 902 can allow the portions to pivot relative to each other about a pin axis. Alternatively, the articulation 120 can include a universal joint. More particularly, the articulation 120 can include a pair of hinges connected by a cross shaft. The universal joint can allow the distal portion of the header assembly 1002 to move with respect to the proximal portion of the header assembly 1002 within several degrees of freedom. For example, the distal portion may pivot about two different planes or axes, in contrast to the single axis of rotation of the barrel hinge 902. Alternative hinge 902 configurations may be incorporated to allow the pacing electrode 106 to engage the septal wall when the housing 108 is directed downward toward the apex of the heart 102.

The hinge 902 may provide movement between portions of the biostimulator 100 during implantation, and can resist relative movement of the portions after implantation. For example, the hinge 902 may have sufficient friction, e.g., between the pin and the header assembly portions, to allow the hinge 902 to resist movement and lock into place when the biostimulator 100 is implanted within heart chamber. The friction may be insufficient, however, to resist implantation forces applied by the transport system, and thus, the biostimulator 100 may be articulated to fit within the heart chamber in an orientation that is maintained by the hinge 902 thereafter.

The portion of the header assembly 1002 distal to the hinge 902 can include a helix mount 1102. The helix mount 1102 can support a fixation helix 1104. More particularly, the fixation helix 1104 can include a helical wire mounted on an outer surface of the helix mount 1102. For example, the helical wire can extend through a helical groove formed in an outer surface of the helix mount 1102. The fixation helix 1104 may extend and/or revolve about electrode axis 112, similar to the helical pacing electrode 106. Accordingly, like the pacing electrode 106, the fixation helix 1104 may be screwed into the target tissue to anchor the header assembly 1002 to the ventricular wall.

The pacing electrode 106 may be radially inward from the fixation helix 1104. In an embodiment, the pacing electrode 106 is independently movable relative to the fixation helix 1104. For example, the pacing electrode 106 may be rotatable relative to the fixation helix 1104. The header assembly 1002 can include an electrode support 1106. Electrode support 1106 can be a post extending along the electrode axis 112 through the helix mount 1102. The post can have an outer surface, e.g., a threaded surface, on which the pacing electrode 106 is located. For example, a distal portion of the post can extend through a center of the pacing electrode 106 such that the helical electrode 302 extends along and grips the outer surface of the electrode support 1106. Accordingly, the pacing electrode 106 can be mounted on the electrode support 1106.

An external threaded surface of the electrode support 1106 may engage in internal threaded surface of the header assembly 1002. For example, the electrode support 1106 can include external square threads that engage corresponding threads of the helix mount 1102. Rotation of electrode support 1106 can cause the threads to interact such that the distal portion of the post moves longitudinally relative to the helix mount 1102. It will be appreciated that, when the pacing electrode 106 is mounted on the electrode support 1106, rotation of the electrode support 1106 can cause a distal tip of the pacing electrode 106 to move longitudinally relative to a distal tip of fixation helix 1104. Similarly, rotation of the electrode support 1106 relative to the helix mount 1102 causes the pacing electrode 106 to rotate relative to the fixation helix 1104. Thus, rotation of electrode support 1106 relative to the helix mount 1102 when the helices are engaged with the target tissue can drive the distal tip of the pacing electrode 106 to a different depth than a depth of the fixation helix 1104. Furthermore, a distance between the distal tips of the fixation helix 1104 and the pacing electrode 106 can be varied. Accordingly, pacing electrode 106 can be driven to any depth needed to engage the target bundle branch 122.

Figure 12:
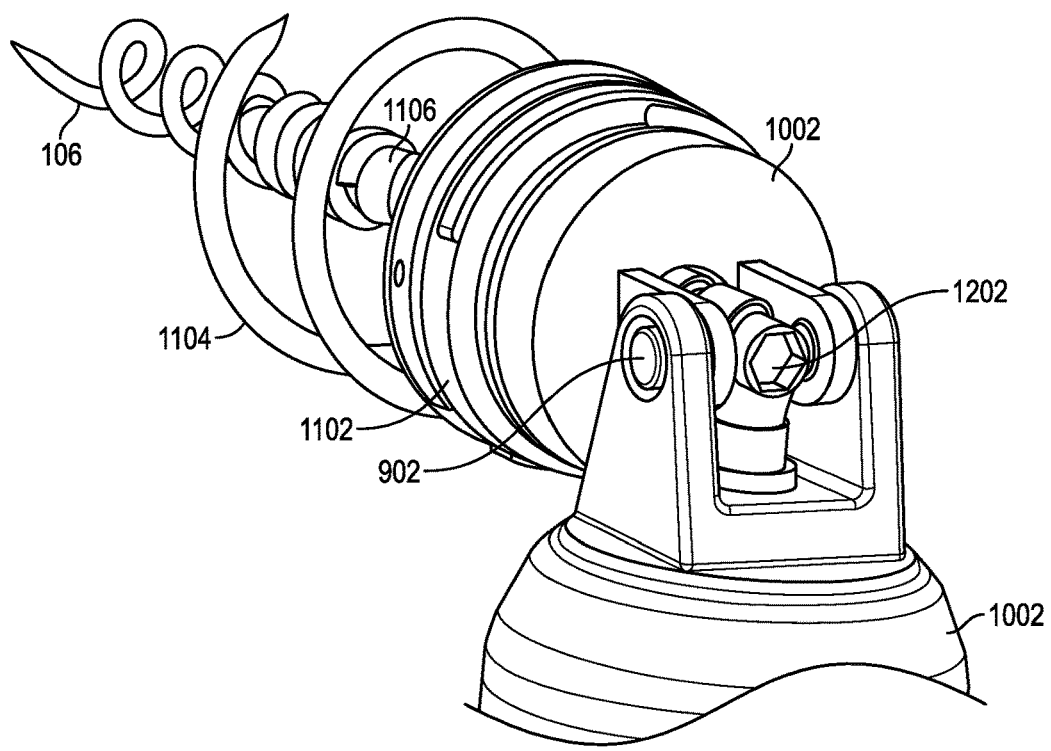
FIG. 12 is a rear perspective view of a distal portion of a biostimulator having an articulable hinge, in accordance with an embodiment.

Referring to FIG. 12, a rear perspective view of a distal portion of a biostimulator having an articulable hinge is shown in accordance with an embodiment. As described above, the pacing electrode 106 can be rotatable relative to other components of the header assembly 1002, e.g., the helix mount 1102. Rotation of the pacing electrode 106 relative to the helix mount 1102 may be affected through a drive mechanism. In an embodiment, the drive mechanism includes a drive socket 1202. For example, the header assembly 1002 can include the drive socket 1202 to receive torque to rotate the pacing electrode 106 relative to the fixation helix 1104. The drive socket 1202 may include a hex socket within which a wrench may be placed to transmit the torque to electrode support 1106. Accordingly, rotation of the drive socket 1202 by a tool can rotate the pacing electrode 106 to a desired depth, independently of the fixation helix 1104.

Figure 13:
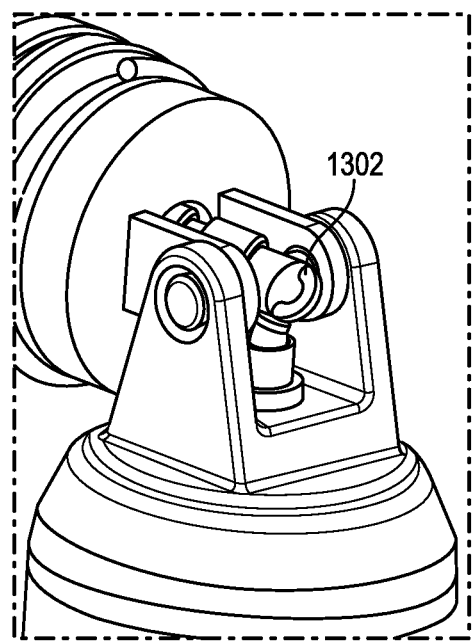
FIG. 13 is a rear perspective view of a distal portion of a biostimulator having an articulable hinge, in accordance with an embodiment.

Referring to FIG. 13, a rear perspective view of a distal portion of a biostimulator having an articulable hinge is shown in accordance with an embodiment. The drive mechanism may incorporate an alternative coupling to transmit torque from a drive tool to the electrode support 1106. For example, the header assembly 1002 can include a drive loop 1302 to receive torque to rotate the pacing electrode 106 relative to the fixation helix 1104. The drive loop 1302 can include a curved bar extending and/or looping back to a distal face of electrode support 1106. The loop can be engaged by a wrench, prong, or another mating structure of a tool to receive torque. More particularly, rotation of the drive loop 1302 about the electrode axis 112 can transmit rotation to the electrode support 1106 and thus to the pacing electrode 106.

Figure 14:
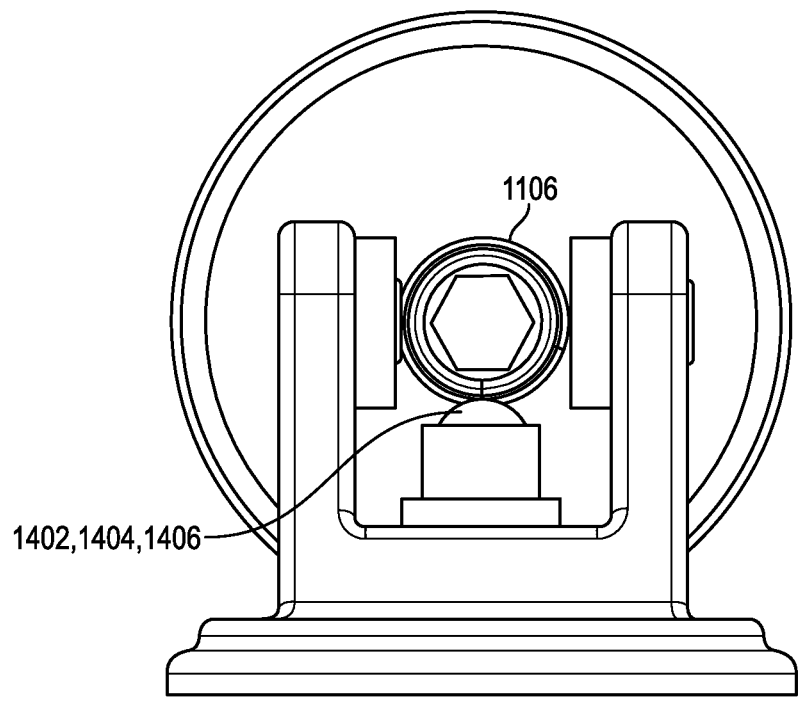
FIG. 14 is a rear view of a distal portion of a biostimulator having an articulable hinge, in accordance with an embodiment.

Referring to FIG. 14, a rear view of a distal portion of a biostimulator having an articulable hinge is shown in accordance with an embodiment. Pacing impulses can be delivered from the pacing circuitry within the electronics compartment 202 to the pacing electrode 106 through the header assembly 1002. In an embodiment, the header assembly 1002 includes an electrical feedthrough 1402 electrically connected to the pacing electrode 106 and to the pacing circuitry. Accordingly, pacing and/or sensing impulses can be transmitted through the electrical feedthrough 1402 from the pacing circuitry to the pacing electrode 106, or vice versa.

In an embodiment, the header assembly 1002 includes an electrical interconnect 1404 between the electronics compartment 202 and the pacing electrode 106. For example, the electrical interconnect 1404 can include a ball plunger 1406 that conducts electrical signals between the pacing circuitry and the pacing electrode 106. For example, the ball plunger 1406 may include a metal ball that receives the pacing impulse. The metal ball may be in contact with a proximal end of the electrode support 1106. For example, the ball of the ball plunger 1406 can contact the drive mechanism of the electrode support 1106. Similarly, the electrode support 1106 can be in electrical contact with the pacing electrode 106, as described above. Thus, the pacing impulse may be delivered from the ball plunger 1406 to the pacing electrode 106 through the electrode support 1106.

Figure 15:
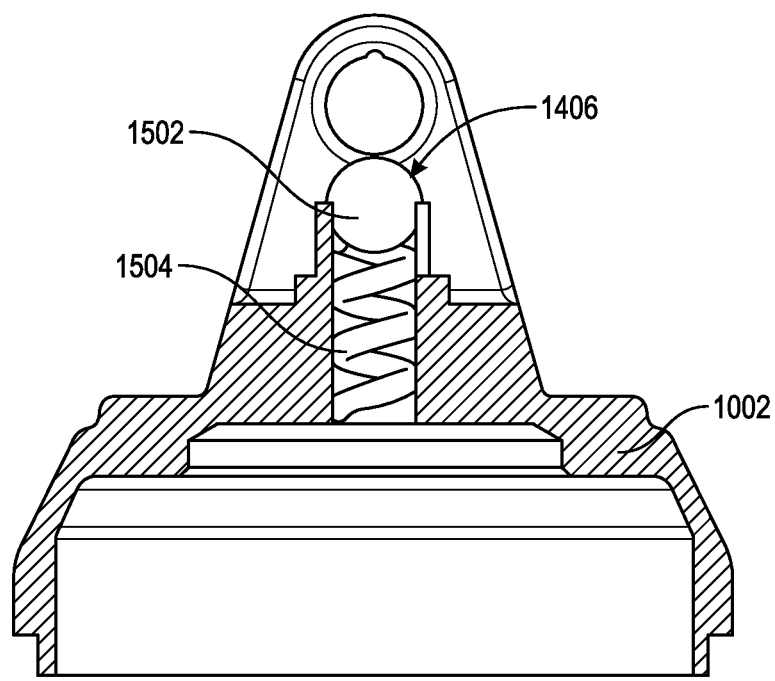
FIG. 15 is a sectional view of a distal portion of a biostimulator having an articulable hinge, in accordance with an embodiment.

Referring to FIG. 15, a sectional view of a distal portion of a biostimulator having an articulable hinge is shown in accordance with an embodiment. In cross-section, the electrical conductivity of the ball plunger 1406 may be understood. The ball plunger 1406 can include the ball 1502 in electrical contact with a spring 1504. The spring 1504 can bias the ball 1502 upward into contact with the electrode support 1106, as shown in FIG. 14. The spring 1504 may extend through a vertical channel within the header assembly 1002 to a proximal end below the ball 1502. The proximal end of the spring 1504 may electrically connect to pacing circuitry contained within the housing 108. For example, an electrical lead may interconnect the pacing circuitry to the proximal end of the spring 1504. Accordingly, the ball 1502 can deflect as required, when the helix mount 1102 rotates about the hinge 902, to provide resilient and consistent electrical contact tween the pacing circuitry and the pacing electrode 106.

Figure 16:
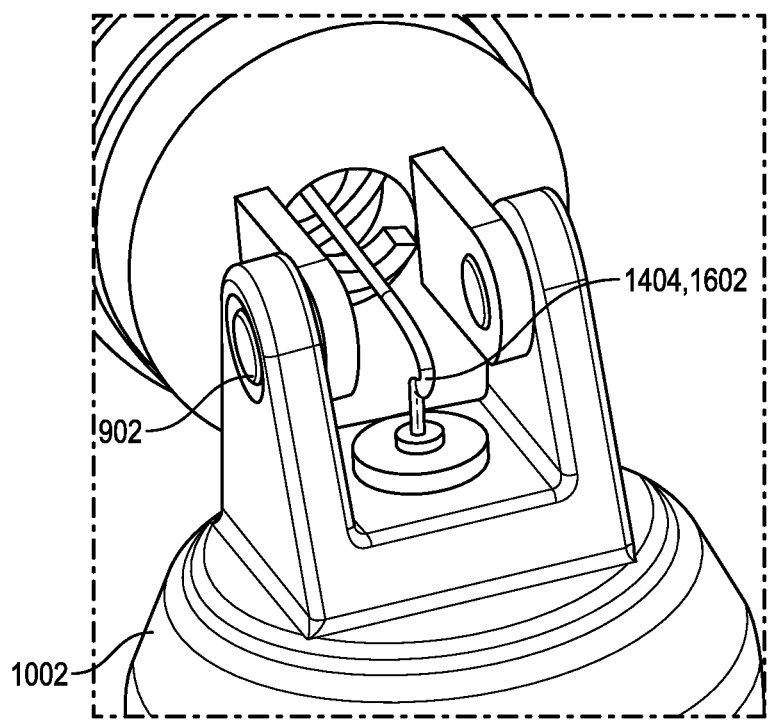
FIG. 16 is a rear perspective view of a distal portion of a biostimulator having an articulable hinge, in accordance with an embodiment.

Referring to FIG. 16, a rear perspective view of a distal portion of a biostimulator having an articulable hinge is shown in accordance with an embodiment. The electrical interconnect 1404 connecting the pacing circuitry to the pacing electrode 106 may be alternatively configured. In an embodiment, the electrical interconnect 1404 includes an electrical lead 1602, e.g., a wire or cable, extending between electronics compartment 202 and the pacing electrode 106. For example, the electrical lead 1602 can extend through a proximal portion of the header assembly 1002 into the housing cavity at a proximal end, and may extend through or into contact with the electrode support 1106 at a distal end. The electrical lead 1602 may therefore conduct pacing impulses from the pacing circuitry contained within the housing 108 to electrode support 1106 and/or the pacing electrode 106. Electrical lead 1602, like the ball plunger 1406, allows for relative movement between the header assembly 1002 portions at the hinge 902 while maintaining electrical conductivity between the pacing circuitry and the pacing electrode 106.

As described above, the pacing electrode 106 may be electrically active to pace the target tissue after implantation. It will be appreciated, however, that the fixation helix 1104 may be electrically active instead of or in addition to the pacing electrode 106. For example, an electrical lead 1602 can interconnect the pacing circuitry to the fixation helix 1104. The fixation helix 1104 may therefore deliver the pacing impulse to tissue when it is implanted within the septal wall. By way of example, fixation helix 1104 may be screwed into the tissue near the right bundle branch and the pacing electrode 106 may be screwed into the tissue by the left bundle branch. Accordingly, each helix may pace a different bundle branch 122 or a different region of the target tissue.

Figure 17:
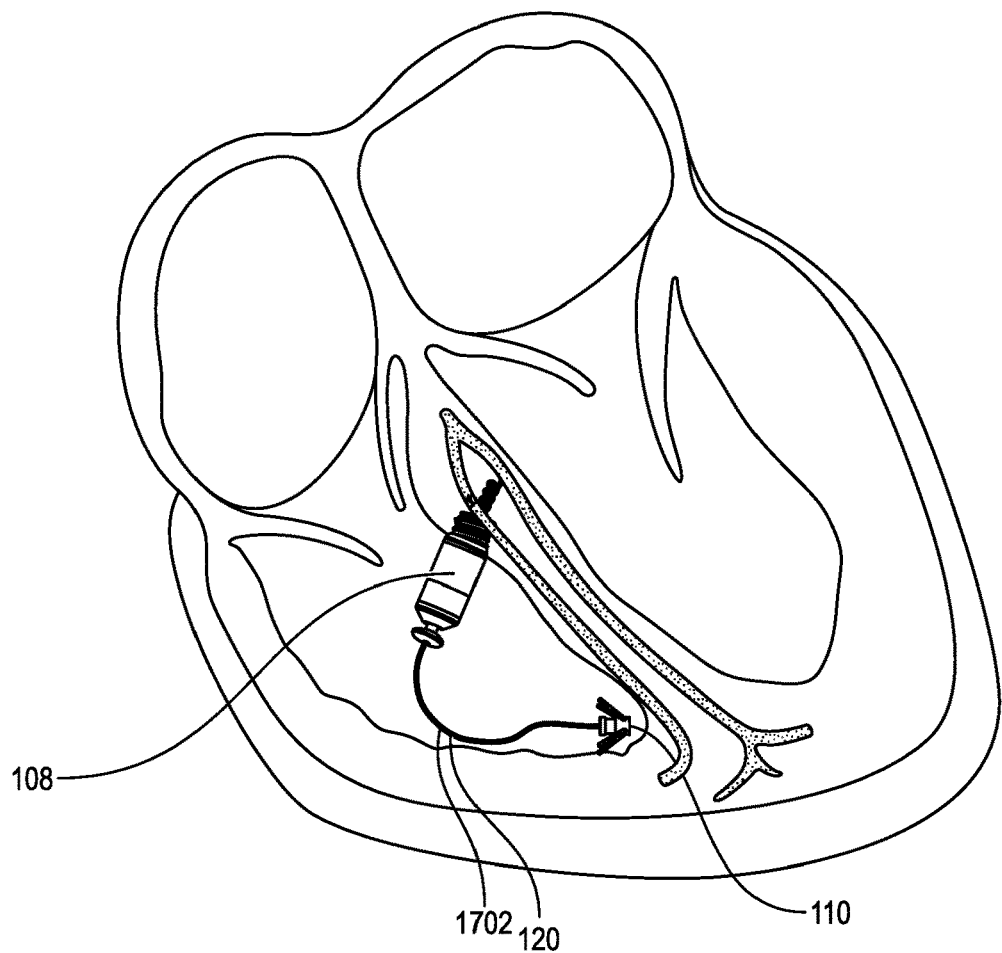
FIG. 17 is a diagrammatic cross section of a patient heart illustrating an example implantation of a biostimulator in a target anatomy, in accordance with an embodiment.

Referring to FIG. 17, a diagrammatic cross section of a patient heart illustrating an example implantation of a biostimulator in a target anatomy is shown in accordance with an embodiment. The articulation 120 of the biostimulator 100 may be located distal or proximal to the housing 108. In embodiment, the articulation 120 includes a tether 1702 extending from the housing 108. For example, the tether 1702 can extend proximately from the attachment feature 230. The anchor 110 may be mounted on the tether 1702, rather than being mounted on the housing 108 or the attachment feature 230, as described above. Accordingly, when the housing 108 is affixed to the septal wall, e.g., by the pacing electrode 106 and/or the fixation helix 1104, the anchor 110 may be affixed to anatomical structures at the apex of the heart 102. The tether 1702 extending between the anchor 110 and the housing 108 may therefore restrain the housing 108 or bias the housing 108 in a downward direction away from an opposite heart wall and/or heart valve. More particularly, the tether 1702 can limit movement of the leadless pacemaker housing 108 to reduce the likelihood that the housing 108 will flip up into engagement with a chamber wall or valve leaflets.

Figure 18:
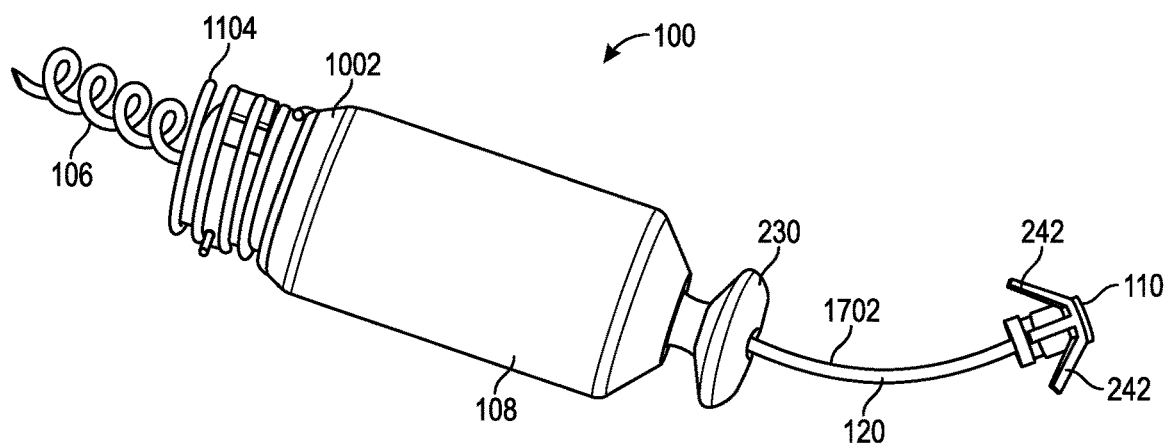
FIG. 18 is a side view of a distal portion of a biostimulator having an articulable tether, in accordance with an embodiment.

Referring to FIG. 18, a side view of a biostimulator having an articulable tether is shown in accordance with an embodiment. The body of the leadless pacemaker may have structure similar to that described above. Biostimulator 100 can include the housing 108 containing pacing circuitry and the attachment feature 230 to engage the transport system during delivery or retrieval. Biostimulator 100 may include the header assembly 1002 mounted on the distal end of the housing 108. In an embodiment, the header assembly 1002 includes the fixation helix 1104. The fixation helix 1104 can screw into the target tissue to anchor the housing 108 to the septal wall. Furthermore, the pacing electrode 106 may be integrated with the header assembly 1002 to deliver the pacing impulse from pacing circuitry to the target tissue. The pacing electrode 106 may include a helical electrode, as described above, a prong electrode or any other electrode shape that engages the septal wall and/or the bundle branch 122 during implantation.

In an embodiment, the tether 1702 is a flexible leash. For example, the tether 1702 can include a cable, e.g., an MP35N or nickel-titanium cable, or wire that is pliable and extends over a length from a distal end at the attachment feature 230 to a proximal end at the anchor 110. Alternatively, the tether 1702 may include a polymer structure, e.g., a polymer cord, filament, wire, or cable. In any case, the tether 1702 can deflect easily at one or more articulations 120 along its length. In the case of a flexible cable, essentially the entire length of the tether can articulate.

A length of the tether 1702 may be selected to allow the tether 1702 to extend from the body of the biostimulator 100, when the biostimulator 100 is affixed to an upper region of the septal wall, into the apex region of the heart chamber. For example, a length of the tether 1702 may be greater than a length of the housing 108. Accordingly, the tether 1702 can interconnect the body of the biostimulator 100 to the anchor 110 affixed at the apex.

The anchor 110 may be attached to the proximal end of the tether 1702. The anchor 110 can have a structure similar to that described above. For example, the anchor 110 may include a central body coupled to the tether 1702, and several tines that extend radially outward from the tether body. The tines 242 may be formed from a soft flexible material such as silicone. Alternatively, the tines 242 may be metallic. In any case, the tines 242 may be resiliently deformed to be loaded into the transport system, and may recover to a larger dimension to entangle within the anatomical structures of the heart 102. When the anchor 110 is entangled within the anatomical structures, it can pull on the tether 1702 to restrain upward movement of the housing 108 and to reduce a likelihood of contact between the body of the biostimulator 100 and the lateral heart wall or the heart valve leaflets.

Figure 19:
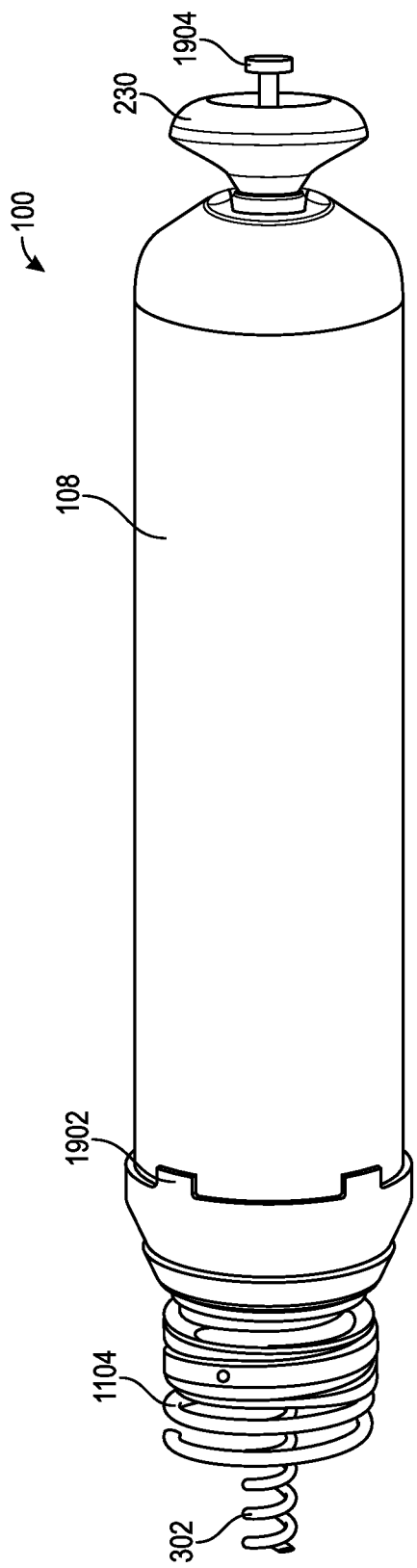
FIG. 19 is a side view of a biostimulator having an independently rotatable pacing electrode, in accordance with an embodiment.

Referring to FIG. 19, a side view of a biostimulator having an independently rotatable pacing electrode is shown in accordance with an embodiment. For bundle branch pacing, e.g., left bundle branch pacing, the depth at which the pacing electrode 106 penetrates the septal wall may be important to effective treatment. More particularly, the pacing electrode 106 may adequately engage the tissue around the target bundle branch 122 to ensure effective pacing. In an embodiment, the biostimulator 100 includes several fixation elements. More particularly, the biostimulator 100 may include the helical electrode 302 and the fixation helix 1104. As described above, the fixation helix 1104 may be used to affix the housing 108 to the septal wall and the helical electrode 302 may deliver the pacing impulse to the target tissue. Given that each of the helical structures is screwed into the heart tissue, a number of rotations that each of the helices requires to engage the tissue may not match. For example, five rotations of the pacing electrode 106 may optimally locate the electrode tip 306 at the left bundle branch 122, however, only two rotations of the fixation helix 1104 may be needed to optimally affix the housing 108 to the target tissue. Accordingly, the ability to rotate the fixation helix 1104 separately from and to a different depth than the pacing electrode 106 may be advantageous.

In an embodiment, the biostimulator 100 includes one or more torque transfer features 1902. The torque transfer features 1902 can include a prong, a protrusion, a nub, or another feature that can be engaged by a tool to transmit torque to the biostimulator body. More particularly, rotation of the torque transfer features 1902 can transmit torque to the housing 108 and the fixation helix 1104. Thus, the torque transfer features 1902 can receive and transmit torque to allow the fixation helix 1104 to be screwed to an appropriate depth within the target tissue.

The pacing electrode 106 may be rotated independently of the fixation helix 1104. In an embodiment, the pacing electrode 106 includes a rotation rod 1904 extending through the biostimulator 100 from the pacing electrode 106. More particularly, the rotation rod 1904 can have a proximal end located proximal to the attachment feature 230 of the biostimulator 100. The proximal end of the rotation rod 1904 can be gripped and rotated by a tool to transmit torque to the pacing electrode 106. Accordingly, pacing electrode 106 can be rotated independently from the fixation helix 1104. The pacing electrode 106 may therefore be screwed to an appropriate depth within the target tissue to effectively pace the target bundle branch 122.

Figure 20:
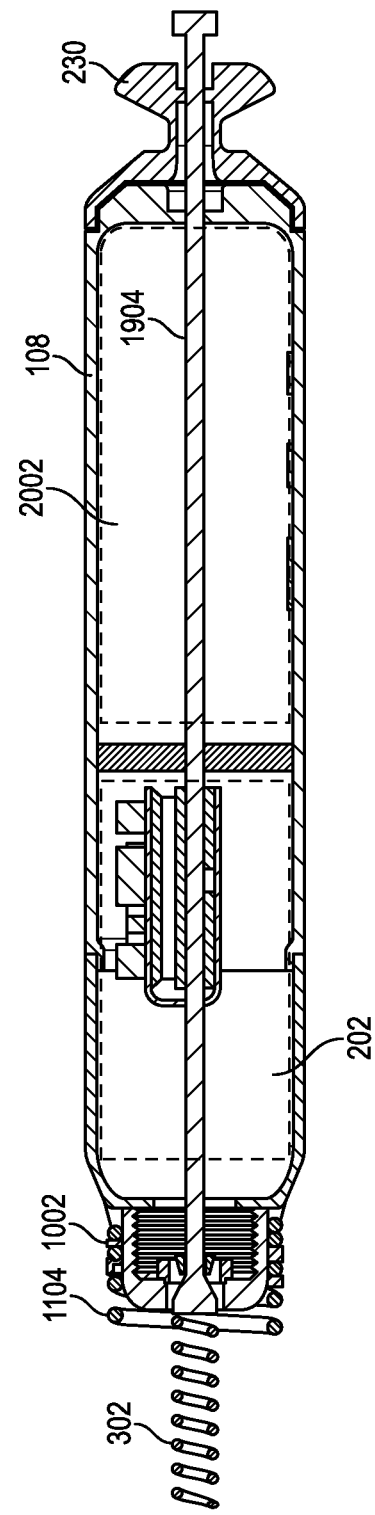
FIG. 20 is a sectional view of a biostimulator having an independently rotatable pacing electrode, in accordance with an embodiment.

Referring to FIG. 20, a sectional view of a biostimulator having an independently rotatable pacing electrode is shown in accordance with an embodiment. The rotation rod 1904 may reside within a hermetically sealed lumen that extends through a center of the biostimulator 100. More particularly, a passage can extend through the attachment feature 230, the housing 108 (including a battery 2002 and the electronics compartment 202), and the header assembly 1002. The rotation rod 1904 can extend through the passage to the pacing electrode 106. Rotation of the rod when the pacing electrode 106 is engaged to the tissue can cause the pacing electrode 106 to screw deeper into the tissue. As the pacing electrode 106 screws into the tissue, the rotation rod 1904 can move axially relative to the body of the biostimulator 100. The fixation helix 1104 may be mounted on the body of the biostimulator 100, and thus, rotation of the rotation rod 1904 causes axial movement of the pacing electrode 106 relative to fixation helix 1104. Accordingly, the pacing electrode 106 and the fixation helix 1104 may be independently set to respective depths within the target tissue.

Figure 21:
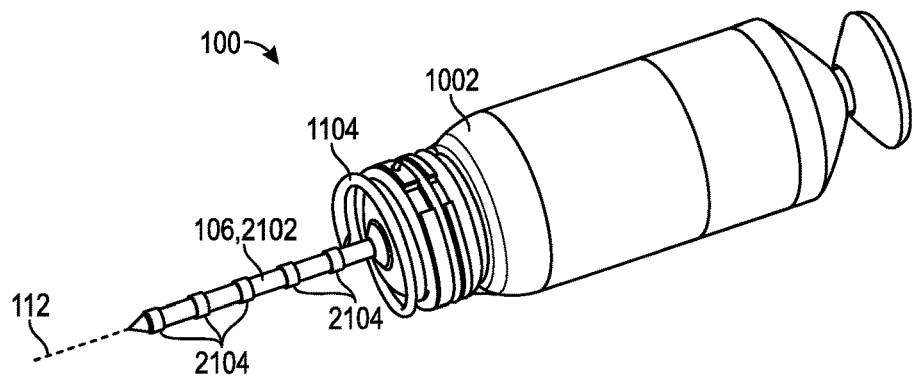
FIG. 21 is a side view of a biostimulator having a post electrode, in accordance with an embodiment.

Referring to FIG. 21, a side view of a biostimulator having a post electrode is shown in accordance with an embodiment. A depth of pacing within the septal wall may be controlled by electrode selection, rather than by varying a depth of a specific electrode. In an embodiment, the pacing electrode 106 includes a post electrode 2102 extending along the electrode axis 112. The post electrode 2102 can include an elongated prong extending longitudinally along the electrode axis 112 to a piercing tip. For example, the piercing tip may be a conical or sharpened tip configured to pierce the septal wall when the biostimulator 100 is delivered. The elongated prong can have a length such that, when the fixation helix 1104 mounted on the header assembly 1002 of the biostimulator 100 is screwed into the target tissue, the piercing tip can extend at least as far as the target bundle branch 122. The piercing tip may extend beyond the target bundle branch 122 after fixation.

In an embodiment, the prong electrode includes one or more electrode bands 2104 mounted on an outer surface of the elongated prong between the helix mount 1102 and the piercing tip. For example, the pacing electrode 106 can include several electrode bands 2104 distributed along the prong length. When the elongated prong is implanted within the target tissue, and the piercing tip extends at least as far as the target bundle branch 122, at least one of the electrode bands may be located near the target bundle branch 122. Accordingly, the optimally located electrode band 2104 may be selected and activated to pace the target bundle branch 122.

The electrode bands 2104 may be independently registrable by circuitry of the biostimulator 100. For example, each electrode band 2104 may be connected to a respective conductor running through the post electrode 2102 and the header assembly 1002 into the electronics compartment 202. The independent conductors can conduct the pacing impulse from the pacing circuitry to the respective electrode band 2104. In an embodiment, multiplexing chips can be used to switch the electrode bands 2104, or portions of the post electrode 2102, on or off. Accordingly, each of the electrode bands 2104 may be controlled by a same chip. Alternatively, each electrode band 2104 may be controlled by a respective chip. Accordingly, the chip(s) can operate to select the electrode band(s) 2104 that are placed in proximity to the target bundle branch 122, and to deliver the pacing impulse to those band(s) through electrical conductors of the header assembly 1002.

Figure 22:
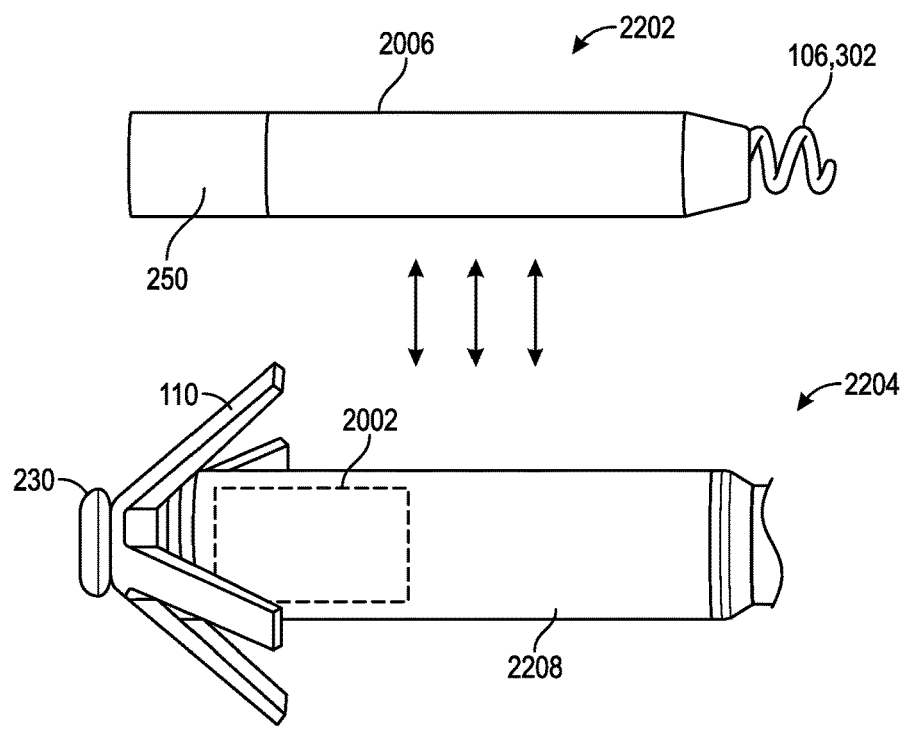
FIG. 22 is a side view of a biostimulator including a housing in wireless communication with a pacing electrode, in accordance with an embodiment.

Referring to FIG. 22, a side view of a biostimulator including a housing in wireless communication with a pacing electrode is shown in accordance with an embodiment. The pacing and sensing signals of the biostimulator 100 may be transferred wirelessly from the pacing circuitry to the pacing electrode 106. In an embodiment, the biostimulator 100 includes a distal module 2202 and a proximal module 2204. The modules may resemble portions of the biostimulator 100 described above. For example, the distal module 2202 can include a distal module housing 2206 having a profile similar to the extension 204. Furthermore, the distal module 2202 can include the pacing electrode 106, e.g., the helical electrode 302. The distal module housing 2206 can contain circuitry to receive wireless signals from the proximal module 2204. The circuitry may transform the wireless signals into the pacing impulse that is then delivered through the pacing electrode 106 to the target bundle branch 122. In an embodiment, the distal module 2202 includes the anode 250. The anode 250 may be mounted at a proximal end of the distal module 2202, spaced apart from the pacing electrode 106 at the distal end of the module.

The proximal module 2204 may include a proximal module housing 2208. The proximal module housing 2208 may be similar to the body of the biostimulator 100 described above. More particularly, the proximal module housing 2208 can contain the electronics compartment 202 and the pacing circuitry. Furthermore, the housing 108 can contain the battery 2002 of the biostimulator 100. Similar to the biostimulator 100 embodiments described above, the proximal module 2204 may include the anchor 110 and/or the attachment feature 230. Accordingly, the proximal module 2204 may be delivered and anchored within the heart chamber in a manner similar to that used for the biostimulator embodiments described above. The distal module 2202 and the proximal module 2204 may operate to deliver the pacing impulse to the target tissue. Unlike biostimulator embodiments described above, however, rather than delivering the pacing impulse through conductors of the extension 204 or the header assembly 1002, pacing impulse is wirelessly transmitted and generated for delivery through the pacing electrode 106.

Figure 23:
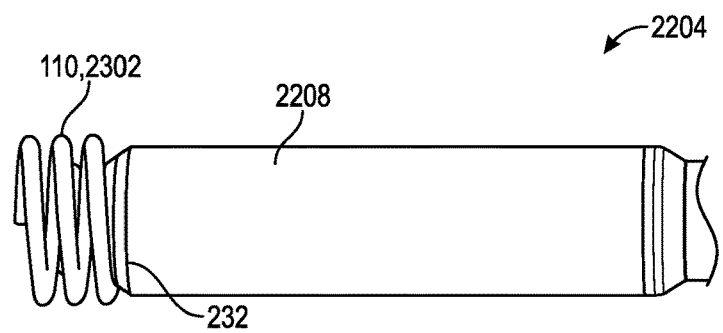
FIG. 23 is a side view of a biostimulator including a housing having a helical anchor, in accordance with an embodiment.

Referring to FIG. 23, a side view of a biostimulator including a housing having a helical anchor is shown in accordance with an embodiment. The proximal module 2204 may include alternative anchoring structures to affix the housing 108 to the heart wall. In an embodiment, the anchor 110 includes a proximal fixation helix 2302 that may be screwed into the heart tissue to secure the housing 108. More particularly, the proximal fixation helix 2302 may be a helical wire mounted on and extending from the housing proximal end 232. The proximal fixation helix 2302 can actively engage tissue of the ventricular apex 105 to stabilize and anchor the proximal module 2204 within the heart 102. By contrast, the distal module 2202 may be delivered to an engaged with the septal wall. Accordingly, the proximal module 2204 near the apex can wirelessly transmit the pacing signal to the distal module 2202 on the septal wall to perform bundle branch pacing.

Figure 24:
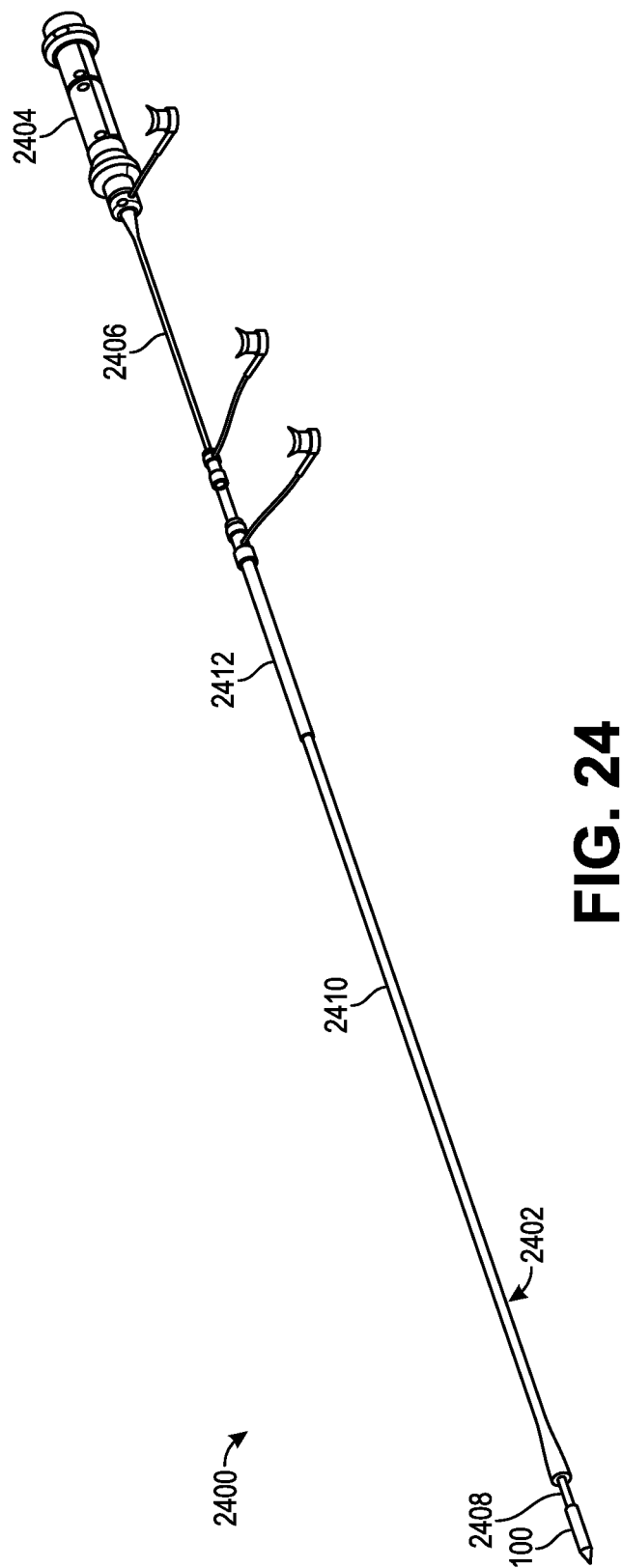
FIG. 24 is a perspective view of a biostimulator system, in accordance with an embodiment.

Referring to FIG. 24, a perspective view of a biostimulator system is shown in accordance with an embodiment. The biostimulator system 2400 can include a biostimulator transport system 2402. The biostimulator transport system 2402 can include a handle 2404 to control movement and operations of the transport system from outside of a patient anatomy. One or more elongated members extend distally from the handle 2404. For example, an outer member 2406 and an inner member 2408 extend distally from the handle 2404. The inner member 2408 can extend through a lumen of the outer member 2406 to a distal end of the transport system. In an embodiment, the biostimulator 100 is mounted on the biostimulator transport system 2402, e.g., at the distal end of one of the elongated members.

The transport system can include a protective sheath 2410 to cover the biostimulator 100 during delivery and implantation. The protective sheath 2410 can extend over, and be longitudinally movable relative to, the elongated members. The transport system may also include an introducer sheath 2412 that can extend over, and be longitudinally movable relative to, the protective sheath 2410. The introducer sheath 2412 can cover a distal end of the protective sheath 2410, the elongated members, and the biostimulator 100 as those components are passed through an access device into the patient anatomy.

Several components of the biostimulator transport system 2402 are described above by way of example. It will be appreciated, however, that the biostimulator transport system 2402 may be configured to include additional or alternate components. More particularly, the biostimulator transport system 2402 may be configured to deliver and/or retrieve the biostimulator 100 to or from the target anatomy.

Figure 25:
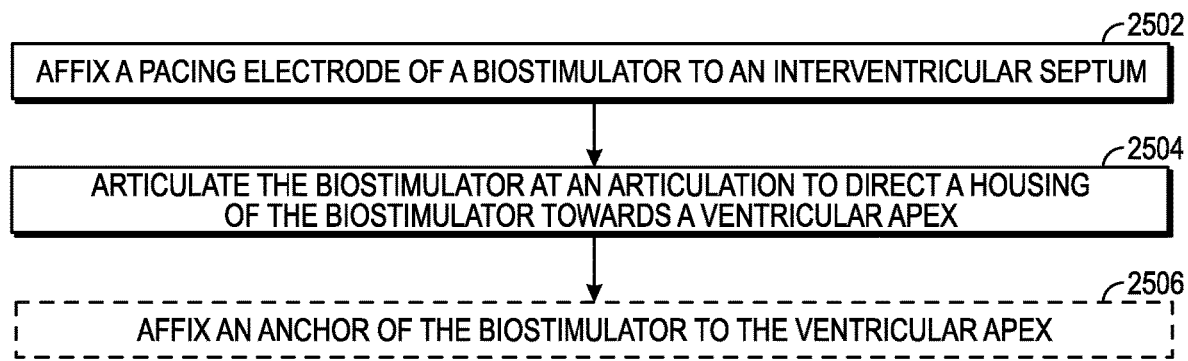
FIG. 25 is a flowchart of a method of implanting a biostimulator for septal pacing, in accordance with an embodiment.

Referring to FIG. 25, a flowchart of a method of implanting a biostimulator for septal pacing is shown in accordance with an embodiment. During the implantation procedure, the biostimulator transport system 2402 can carry the biostimulator 100 into the target heart chamber. When implantation is to be within the right ventricle, the biostimulator transport system 2402 can be tracked through the inferior vena cava into the right atrium and across the tricuspid valve into the right ventricle. The distal end of the transport system can be steered toward a desired location of the septal wall. For example, the target area may be in an upper region of the interventricular septal wall 104.

At operation 2502, the pacing electrode 106 may be affixed to the interventricular septum. When a distal end of the biostimulator 100 is in contact with the septal wall, torque can be transferred from the biostimulator transport system 2402 to the biostimulator 100, e.g., via the attachment feature 230. Rotation of the biostimulator 100 can drive the pacing electrode 106 and/or the fixation helix 1104 into the septal tissue. Alternatively, the electrode support 1106 may be rotated via the drive mechanism in some embodiments to cause the pacing electrode 106 to screw into the target tissue. More particularly, the pacing electrode 106 and/or the fixation helix 1104 can be screwed into the tissue to a desired depth by rotating the helices into the target tissue. The pacing electrode 106 may engage the tissue at a depth that allows effective pacing of the target bundle branch 122.

At operation 2504, the biostimulator 100 may be articulated at the articulation 120. For example, the biostimulator transport system 2402 can be placed in a tether mode that allows the attachment feature 230 to interconnect to the elongated members by flexible cables, without requiring the biostimulator 100 to be directly engaged to the protective sheath 2410 or the elongated members. In the tether mode, the proximal portion of the biostimulator 100 can be deflected downward toward the ventricular apex 105. More particularly, the extension 204 of the biostimulator 100 can be bent, the hinge 902 may be pivoted, or any other articulation 120 may be actuated to direct the housing 108 of the biostimulator 100 toward the ventricular apex 105.

At operation 2506, optionally, an anchor 110 of the biostimulator 100 may be affixed at the ventricular apex 105. More particularly, the anchor 110 can engage with trabeculae carneae on an internal surface of the myocardium, or another heart structure. The anchor 110 may include flexible tines 242 arranged about an anchor axis 244, as described above, and the tines 242 may engage the heart structure. Accordingly, the anchor 110 can achieve fixation and stabilization of the housing 108 to reduce a likelihood that the housing 108 will interfere with the heart wall or the heart valve while the pacing electrode 106 paces the target bundle branch 122.

It will be appreciated that the operations described above may be performed in any order. For example, the order described above may be a forward implant procedure in which the pacing electrode 106 is engaged to the septal wall before directing the housing 108 toward the apex. In an alternative embodiment a backward implant procedure may be used. In the backward implant procedure, the housing 108 of the biostimulator 100 may first be placed at the apex. The articulation 120 may then be articulated to direct the pacing electrode 106 toward the septal wall. The pacing electrode 106 and/or the fixation helix 1104 may then be screwed into the septal wall to engage the target tissue.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator, comprising:
   a housing having an electronics compartment containing pacing circuitry, wherein the housing includes a housing axis;
   a header assembly including a proximal portion mounted on the housing and a pacing electrode mounted on a distal portion, wherein the pacing electrode is electrically connected to the pacing circuitry, and wherein the pacing electrode has an electrode axis; and
   a hinge including a pin rotatably coupling the distal portion to the proximal portion such that, when the pacing electrode is affixed to an interventricular septal wall and the housing is located at a ventricular apex, the electrode axis and the housing axis extend in different directions.

2. The biostimulator of claim 1, wherein the pacing electrode includes a helical electrode extending about the electrode axis.

3. The biostimulator of claim 1, wherein the pacing electrode includes a post electrode extending along the electrode axis.

4. The biostimulator of claim 1, wherein the header assembly includes an electrical feedthrough electrically connected to the pacing electrode and the pacing circuitry.

5. The biostimulator of claim 4 further comprising an electrical interconnect between the electronics compartment and the header assembly.

6. The biostimulator of claim 5, wherein the electrical interconnect includes an electrical lead.

7. The biostimulator of claim 5, wherein the electrical interconnect includes a ball plunger.

8. The biostimulator of claim 4, wherein the pacing electrode is rotatable relative to the header assembly.

9. The biostimulator of claim 8, wherein the header assembly includes a drive socket to receive torque to rotate the pacing electrode relative to a fixation helix.

10. The biostimulator of claim 8, wherein the header assembly includes a drive loop to receive torque to rotate the pacing electrode relative to a fixation helix.

11. The biostimulator of claim 1, wherein the hinge includes a universal joint.

12. The biostimulator of claim 1 further comprising a fixation helix extending about the electrode axis, wherein the pacing electrode is radially inward from the fixation helix.

13. A biostimulator system, comprising:
    a biostimulator transport system; and
    a biostimulator mounted on the biostimulator transport system, wherein the biostimulator includes a housing having an electronics compartment containing pacing circuitry, a header assembly including a proximal portion mounted on the housing and a pacing electrode mounted on a distal portion, wherein the pacing electrode is electrically connected to the pacing circuitry, and a hinge including a pin rotatably coupling the distal portion to the proximal portion such that, when the pacing electrode is affixed to an interventricular septal wall and the housing is located at a ventricular apex, an electrode axis of the pacing electrode extends in a different direction than a housing axis of the housing.

14. The biostimulator system of claim 13, wherein the pacing electrode includes one or more of a helical electrode extending about the electrode axis or a post electrode extending along the electrode axis.

15. A method, comprising:
    affixing a pacing electrode of a biostimulator to an interventricular septum; and
    articulating a biostimulator at an articulation to direct a housing of the biostimulator toward a ventricular apex such that an electrode axis of the pacing electrode extends in a different direction than a housing axis of the housing, wherein the biostimulator includes the housing having an electronics compartment containing pacing circuitry, a header assembly including a proximal portion mounted on the housing and the pacing electrode mounted on a distal portion, wherein the pacing electrode is electrically connected to the pacing circuitry, and a hinge including a pin rotatably coupling the distal portion to the proximal portion.

16. The method of claim 15, wherein the pacing electrode includes one or more of a helical electrode extending about the electrode axis or a post electrode extending along the electrode axis.

\* \* \* \* \*